United States Patent
Sealfon

(10) Patent No.: US 6,575,946 B2
(45) Date of Patent: Jun. 10, 2003

(54) PORTABLE ASPIRATING DEVICE WITH ANTI-SPLASH BAFFLE

(76) Inventor: Andrew I. Sealfon, 24 Carpenter Rd., Chester, NY (US) 10918

(*) Notice: Subject to any disclaimer, the term of this patent is extended or adjusted under 35 U.S.C. 154(b) by 168 days.

(21) Appl. No.: 09/835,174

(22) Filed: Apr. 16, 2001

(65) Prior Publication Data

US 2002/0148465 A1 Oct. 17, 2002

(51) Int. Cl.$^7$ .................................................. A61M 1/00
(52) U.S. Cl. ....................................................... 604/323
(58) Field of Search ............................. 604/317–326, 604/406, 540, 541

(56) References Cited

U.S. PATENT DOCUMENTS

| | | | | |
|---|---|---|---|---|
| 3,685,517 A | * | 8/1972 | Reynolds et al. ............ | 128/277 |
| 4,256,109 A | * | 3/1981 | Nichols ........................ | 128/276 |
| 4,275,731 A | * | 6/1981 | Nichols ........................ | 128/276 |
| 4,681,571 A | * | 7/1987 | Nehring ....................... | 604/320 |
| 4,880,411 A | * | 11/1989 | Fangrow, Jr. et al. ........ | 604/149 |
| 5,759,396 A | * | 6/1998 | Van Driel .................... | 210/315 |

OTHER PUBLICATIONS

GEN/PORE Porous Poly Product Data Sheet by General Polymeric Corp.
What is the first thing you'll reach for in many emergencies? . . . by Repro–Med Systems, Inc.

* cited by examiner

Primary Examiner—Weilun Lo
Assistant Examiner—Michael Bogart
(74) Attorney, Agent, or Firm—Myron Amer, P.C.

(57) ABSTRACT

A portable aspiration device using suction to clear a breathing obstacle or the like in conjunction with a commercially available flow-control member providing opposing operating mode objectives of progressively diminishing porosity in response to fluid contact and progressively increasing the volume of aspirated fluid in a reservoir so that ideally suction is cut off when the reservoir is full to avoid overflow, but in which assumed positions during use inadvertently cause splashing contact of fluid against the flow-control member and premature suction cut off by an unfilled reservoir to interrupt treatment. As a solution, a baffle in size and shape is disposed about the flow-control member and adjacent facing surfaces bound therebetween a compartment of such nominal width that splashing does not occur therein.

1 Claim, 2 Drawing Sheets

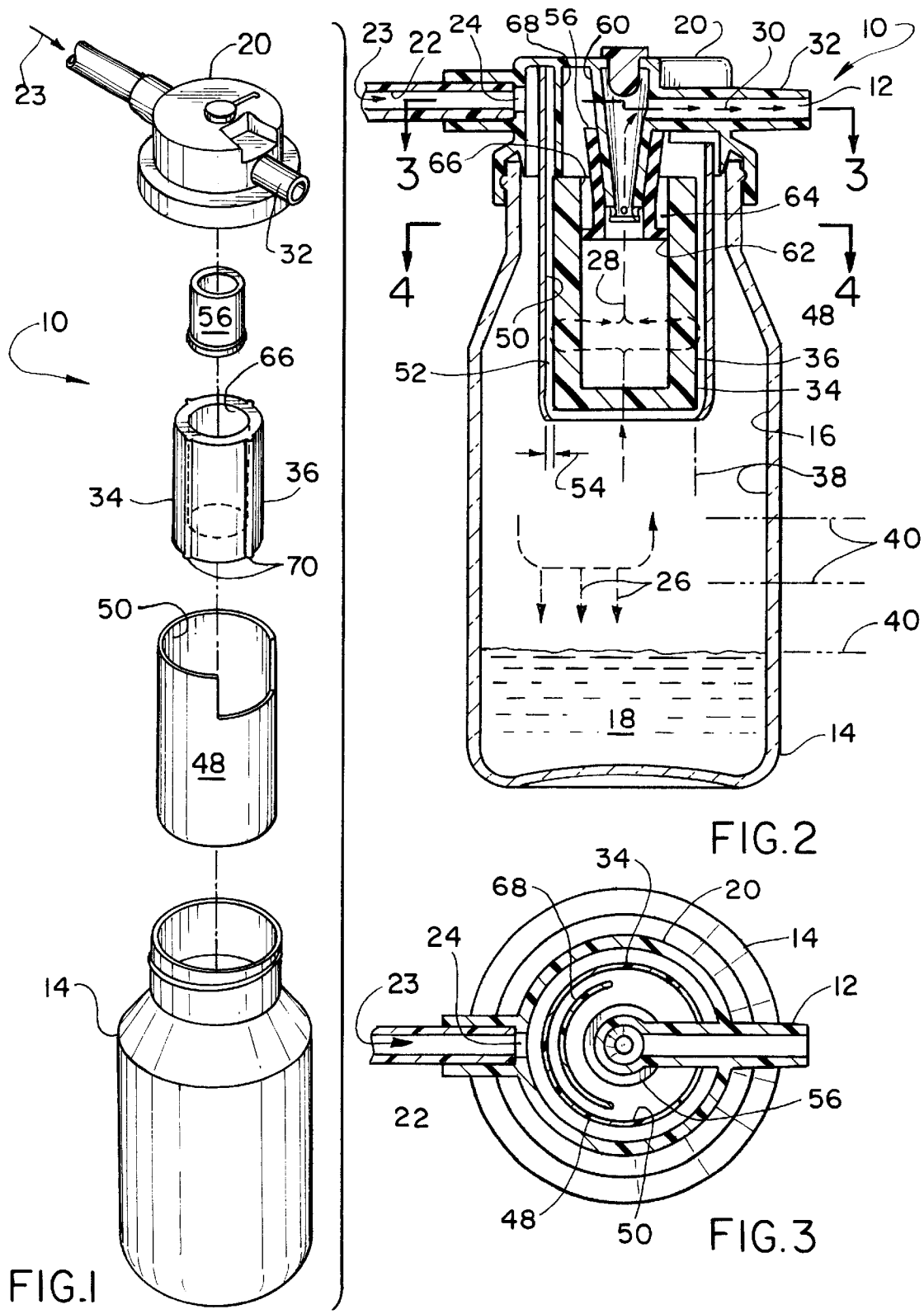

PORTABLE ASPIRATING DEVICE WITH ANTI-SPLASH BAFFLE

BACKGROUND OF THE INVENTION

The present invention relates generally to the application of emergency suction as provided by paramedics in ambulances or during air medivac transports, or by first responders at emergencies for which airway suction is required, as well as for suctioning infants during childbirth or for other pediatric emergencies, to mention but a few examples of end uses.

1. Field of the Invention

There is a need for the application of suction to clear breathing obstacles and it is advantageous to do so, using a suction pump in cojoint operation with an aspiration device during which a fluid air mixture, which typically is the consistency of the breathing obstacle to be cleared, to be removed by the suction along a flow path along which there is released from the mixture the fluid content thereof into a reservoir, and there is continued flow of the remaining air content to the site of suction, i.e., the vacuum pump. During the operating mode as just generally described, it is important for reasons well understood that the suction pump does not get contaminated with vomitus and/or other body fluids. Also, excess fluid which is suctioned should not be allowed to drop out the exhaust of the pump to contaminate the health care provider, who normally would be covered with body fluids dripping from the pump after it aspirates excess fluid.

2. Description of the Related Art Including Information Disclosed Under 37 CFR 1.98

Literature entitled "What Is The First Thing You Will Reach For In Many Emergencies? . . . " describing a hand-activated vacuum pump sold under the designation RES-Q-VAC constructed to have an operating mode of producing a negative or vacuum pressure providing a pressure gradient for directional flow through an aspirating device according to the present invention from a source of removal of mucous or like material from a patient to the vacuum pump or suction site.

Literature entitled "Sporous Poly" sold under the designation GEN/PORE having the known unique properties of allowing air to flow through it but solidifies when any fluid impinges upon the material, and it becomes totally blocked preventing any liquid from passing through it.

BRIEF SUMMARY OF THE INVENTION

The invention consist of the application of the GEN/PORE air flow material to a portable, hand-held suction device, and achieving the enormous benefits of the portable solution of the application by providing a strategically located baffle in operative relation to the GEN/PORE material to minimize inadvertent liquid from decreasing the suction performance of the system until the reservoir is full, as will be better understood as the description proceeds.

BRIEF DESCRIPTION OF THE SEVERAL VIEWS

The description of the drawings of the invention which follows, together with the accompanying drawings should not be construed as limiting the invention to the example shown and described, because those skilled in the art to which this invention appertains will be able to devise other forms thereof within the ambit of the appended claims.

FIG. 1 is an exploded perspective view of the components of the aspirating device according to the present invention;

FIG. 2 is a side elevational view in longitudinal cross section of the FIG. 1 device in assembled condition;

Figures 4, 5:
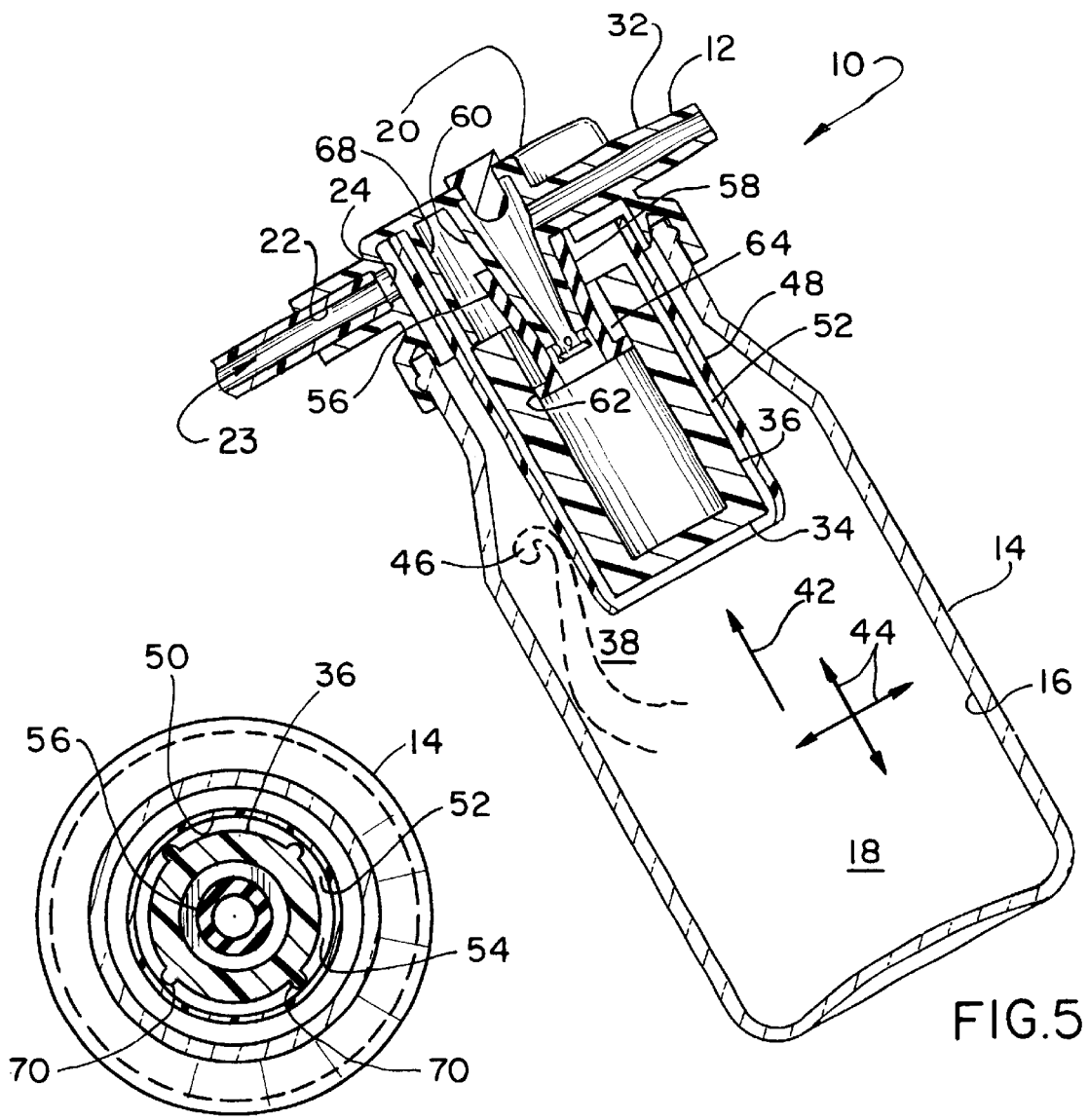

FIGS. 3 and 4 are sectional views taken along lines 3—3 and 4—4 of FIG. 2; and

FIG. 5 is a view similar to FIG. 2 but illustrating the device in a typical position of use.

DETAILED DESCRIPTION OF THE INVENTION

The construction and operating mode of the aspirating device, generally designated 10 in FIGS. 2 and 5, are best understood in conjunction with the exploded view of FIG. 1 to which reference also should now be made. For providing vacuum service to the device 10 use is preferably made of a hand-activated vacuum pump (not shown) selected from one of many such pumps of known construction and operating mode and sold commercially, such as the one sold under the designation RES-Q-VAC hand powered emergency suction and commercially available from Repro-Med Systems, Inc. of Chester, N.Y. 10918, the known construction and operating mode to be producing a negative or vacuum pressure providing a pressure gradient for directional flow through the device from a source of removal of mucous or like material from a patient to the vacuum pump or suction site 12.

One component used is a cylindrical container 14, preferably a glass bottle, having an inner surface 16 bounding an aspirating fluid reservoir 18. A cap 20 is provided for the container 14 and has in attached laterally extending relation therefrom for a fluid air mixture 23 an intake 22 opening, as at 24, into the reservoir 18 for releasing from the mixture the fluid content 26 thereof and continuing the flow, as noted by the arrow 28 of the air content 30 thereof into an exit conduit 32 in attached laterally extending relation also from the cap 20.

Another component is a cylindrical flow-control member 34 in depending attached relation from the cap 20 and in an operative interposed position between the intake 22 and exit conduit 32 of varying porous construction material, of known functioning in response to fluid contact and commercially available from General Polymeric Corp. of Reading, Pa. 19607 sold under the designation GEN/PORE-identified porous poly, the known unique properties of which is that it allows air to flow through but solidifies when any fluid impinges upon the material, and it becomes totally blocked preventing any liquid from passing through it. GEN/PORE porous poly is known to be used in large suction systems to prevent overflow, but is not known to have ever been adapted to a portable, hand-held, non-electric suction device such as the RES-Q-VAC device which is subjected to various positions and motions which large suction containers are not subjected. For the application in accordance with the present invention, it is pertinent to note that flow-control member 34 has an outer surface 36 in facing relation to the inner surface 16 of the container 18 and said inner and outer surfaces 16, 36 bounding therebetween a flow path 38 between the intake 22 and exit conduit 32.

Under favorable conditions of use, the porosity of the flow-control member 34 will diminish upon contact with rising levels, individually and collectively designated 40 of aspirated fluid released into the reservoir 18 until the container 14 is full signaling the need to replace the container 14 to prevent overflow and the release of aspirated fluid contaminating the treatment area and subjecting individuals in the area to health hazards.

However, an unfilled container 14 due to angular positions 42 and lateral/vertical movements 44, as depicted in FIG. 5, might produce fluid splashing, as denoted at 46, against the flow-control member 34 particularly in the flow path 38 which would block air flow to the suction site 12 because of diminished porosity in the construction material of the flow-control member 34, and thus interrupt the treatment being administered to a patient such as during transport to a medical facility in an ambulance.

Obviating unnecessary replacement of an unfilled container 14 is the patentable advance of the device 10 and is achieved using as a component a cylindrical hollow baffle 48 mounted in depending relation from the cap 20 and in encircling relation about the flow-control member 34 having an inner surface 50 in facing relation to the outer surface 36 of the flow-control member 34 and such inner and outer surfaces 50, 36 bounding therebetween a splash-inhibiting compartment 52 subdividing the flow path 38 between the intake 22 and exit conduit 32 characterized by a width 54 of a selected nominal extent to obviate any fluid splashing phenomenon therein. As a consequence angular positions 40 and lateral/vertical movements 44 of the aspirating device 10 during use do not result in fluid contact with the flow-control member 34 of an extent as might occur in an unfilled but progressively being filled reservoir 18 without a subdivided flow path 38.

For completeness sake, it is noted that in a preferred embodiment use is made of a hollow rubber adapter 56 expanded into a conical shape 58 and frictionally attached to a depending extension 60 of the cap 20 and is seated, as at 62, below a collar 64 adhesively secured in the upper opening 66 of the flow-control member 34 to hold the flow-control member 34 in its operative position as illustrated. Also provided is a fixed baffle 68 integrally molded as depending structure of the cap 20.

Lastly, of some significance but nevertheless optional, the outer surface of the flow-control member 34 is provided with circumferentially spaced apart standoff ribs 70 to contribute in maintaining the compartment 52 open for air flow therethrough.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A hand-activated vacuum pump providing vacuum pressure for an aspirating device comprising a cylindrical container having an inner surface bounding an aspirating fluid reservoir, a cap for said container having in a laterally attached extending relation therefrom a fluid air mixture intake into said reservoir for releasing from said fluid air mixture the fluid content thereof and continuing the flow of said air content thereof into an exit conduit in a laterally attached extending relation also from said cap, a cylindrical flow-control member in depending attached relation from said cap and in an operative interposed position between said intake and said exit conduit, said cylindrical flow-control member being of a construction material that varies in porosity in response to fluid contact being made therewith and said cylindrical flow-control member in said operative interposed position having an outer surface in facing relation to said inner surface of said cylindrical container and said outer and inner surfaces respectively of said flow-control member and said cylindrical container bounding therebetween a flow path between said intake and exit conduit, and a cylindrical hollow baffle mounted in depending relation from said cap and in encircling relation about said flow-control member, said cylindrical hollow baffle having an inner surface in facing relation to said outer surface of said flow-control member and said inner and outer surfaces respectively of said baffle and said flow-control member bounding therebetween a splash-inhibiting compartment subdividing said flow path between said intake and exit conduit characterized by a width selected to obviate any fluid splashing phenomenon therein, whereby angular positions and lateral/vertical movements of said aspirating device during use do not result in fluid contact with said flow-control member of an extent as might occur in an unfilled but progressively filling reservoir without a subdivided flow path.

* * * * *